(12) United States Patent
Uske et al.

(10) Patent No.: US 11,508,479 B2
(45) Date of Patent: Nov. 22, 2022

(54) AUTOMATED QUESTION GENERATION AND RESPONSE TRACKING

(71) Applicant: Optum, Inc., Minnetonka, MN (US)

(72) Inventors: Kathleen Elizabeth Uske, Old Bridge, NJ (US); Kelsey Lucinda Isenberg, Indiana, PA (US)

(73) Assignee: Optum, Inc., Minnetonka, MN (US)

(*) Notice: Subject to any disclaimer, the term of this patent is extended or adjusted under 35 U.S.C. 154(b) by 0 days.

(21) Appl. No.: 16/158,658

(22) Filed: Oct. 12, 2018

(65) Prior Publication Data

US 2019/0115104 A1    Apr. 18, 2019

Related U.S. Application Data

(60) Provisional application No. 62/572,840, filed on Oct. 16, 2017.

(51) Int. Cl.
*G16H 50/20* (2018.01)
*G06V 40/20* (2022.01)
(Continued)

(52) U.S. Cl.
CPC ............ *G16H 50/20* (2018.01); *G06F 3/167* (2013.01); *G06F 11/3438* (2013.01); *G06V 40/20* (2022.01); *G16H 10/20* (2018.01)

(58) Field of Classification Search
CPC ........ G16H 50/20; G16H 10/20; G06F 3/167; G06F 11/3438; G06K 9/00335; G06Q 50/22–24; G06Q 50/20–26
(Continued)

(56) References Cited

U.S. PATENT DOCUMENTS 4,770,636 A * 9/1988 Buschke .................. G09B 7/02
                                                434/236
5,230,629 A * 7/1993 Buschke ................ G09B 19/00
                                                273/454
(Continued)

FOREIGN PATENT DOCUMENTS

CA        2809827 A1 *  3/2012  ......... A61B 5/04842
WO   WO-2006066105 A2 *  6/2006  ............. A61B 5/16
WO   WO-2006088415 A1 *  8/2006  ........... A61B 5/1124

OTHER PUBLICATIONS

Jacobs, Jules. "Determining hot items with exponentially decaying likes". 2015. Mostly Programming, all pages. julesjacobs.github.io/2015/05/06/exponentially-decaying-likes.html (Year: 2015).*
(Continued)

*Primary Examiner* — Jason S Tiedeman
*Assistant Examiner* — Jessica Marie Webb
(74) *Attorney, Agent, or Firm* — Alston & Bird LLP

(57) ABSTRACT

There is a need for solutions that monitor memory loss with reduced caretaker involvement. This need can be addressed by, for example, selecting a first question from a group of multiple questions to ask a user of a computing device based one or more attributes associated with each question in the group of multiple questions; receiving a first answer by the user of the computing device to the first question; determining, from the first answer, one or more behavioral attributes associated with user response to the first question; and determining, based on the one or more behavioral attributes, a cognitive capability of the user of the computing device.

19 Claims, 6 Drawing Sheets

(51) Int. Cl.
*H04L 67/54* (2022.01)
*G06F 3/16* (2006.01)
*G16H 10/20* (2018.01)
*G06F 11/34* (2006.01)

(58) Field of Classification Search
USPC .................................................. 705/2
See application file for complete search history.

(56) References Cited

U.S. PATENT DOCUMENTS

| | | | | |
|---|---|---|---|---|
| 5,911,581 | A * | 6/1999 | Reynolds | A61B 5/16 434/236 |
| 6,364,666 | B1 * | 4/2002 | Jenkins | G09B 5/04 434/156 |
| 10,272,294 | B2 * | 4/2019 | Williams | G06F 3/0481 |
| 10,874,355 | B2 * | 12/2020 | Vaughan | G16H 50/70 |
| 2002/0017994 | A1 * | 2/2002 | Balkin | A61B 5/16 340/573.1 |
| 2003/0036683 | A1 * | 2/2003 | Kehr | G06F 19/325 600/300 |
| 2004/0152995 | A1 * | 8/2004 | Cox | A61B 5/048 600/544 |
| 2009/0240522 | A1 * | 9/2009 | Handal | G06F 19/3418 705/2 |
| 2010/0092929 | A1 * | 4/2010 | Hallowell | G16H 50/30 434/167 |
| 2011/0264465 | A1 * | 10/2011 | Lindsay | G16H 40/67 705/2 |
| 2012/0232931 | A1 * | 9/2012 | Buisman | G16H 40/63 705/3 |
| 2013/0132110 | A1 * | 5/2013 | Nagaoka | G06F 19/3481 705/2 |
| 2014/0099625 | A1 * | 4/2014 | Gennuso | G06Q 10/10 434/350 |
| 2014/0278474 | A1 * | 9/2014 | McClure | G16H 10/20 705/2 |
| 2015/0356144 | A1 * | 12/2015 | Chawla | G06N 5/04 707/741 |
| 2016/0048648 | A1 * | 2/2016 | Sanchez | G06F 19/00 706/12 |
| 2016/0125748 | A1 * | 5/2016 | Ashford | G16H 15/00 434/236 |
| 2016/0132773 | A1 * | 5/2016 | Chandrasekaran | G06N 5/04 706/11 |
| 2016/0171392 | A1 * | 6/2016 | Allen | G06F 16/90332 706/11 |
| 2016/0196389 | A1 * | 7/2016 | Moturu | G16H 50/20 705/2 |
| 2016/0210442 | A1 * | 7/2016 | Ethington | G16H 10/20 |
| 2017/0140114 | A1 * | 5/2017 | Are | G16H 50/20 |
| 2017/0372020 | A1 * | 12/2017 | Govro | G16H 40/20 |
| 2018/0322961 | A1 * | 11/2018 | Kim | A61B 5/4803 |
| 2019/0043610 | A1 * | 2/2019 | Vaughan | A61B 5/4088 |
| 2019/0065403 | A1 * | 2/2019 | Zaydman | G06F 12/0895 |
| 2019/0066834 | A1 * | 2/2019 | Tuyl | A61M 21/02 |
| 2019/0167179 | A1 * | 6/2019 | Arzy | A61B 5/7475 |

OTHER PUBLICATIONS

Ho, Ricky. "Pragmatic Programming Techniques: Characteristics of Machine Learning Model". 2012. Blogspot, all pages. horicky.blogspot.com/2012/02/characteristics-of-machine-learning.html (Year: 2012).*

Rabelo, Luis et al. "Development of a Real-Time Learning Scheduler using Reinforcement Learning Concepts". 1994. 1994 IEEE International Symposium on Intelligent Control, all pages. pp. 291-296. https://ieeexplore.ieee.org/stamp/stamp.jsp?tp=&arnumber=367802 (Year: 1994).*

Kotsiantis, SB et al. "Supervised Machine Learning: A Review of Classification Techniques". 2007. Informatica 31 (2007) 249-268. all pages. https://datajobs.com/data-science-repo/Supervised-Learning-[SB-Kotsiantis].pdf (Year: 2007).*

N.a.), "movmean", Aug. 2, 2016, MathWorks, R2016a Documentation, all pages, Retrieved from Wayback Archive: https://web.archive.org/web/20160802053448/https://www.mathworks.com/help/matlab/ref/movmean.html (Year: 2016).*

H. Tanaka et al., "Detecting Dementia Through Interactive Computer Avatars," in IEEE Journal of Translational Engineering in Health and Medicine, vol. 5, pp. 1-11, Sep. 15, 2017, Art No. 2200111, doi: 10.1109/JTEHM.2017.2752152. (Year: 2017).*

S. Joshi, P. Deepa Shenoy, V. K R and L. M. Patnaik, "Evaluation of different stages of dementia employing neuropsychological and machine learning techniques," 2009 First International Conference on Advanced Computing, 2009, pp. 154-160, doi: 10.1109/ICADVC.2009.5378199. (Year: 2009).*

* cited by examiner

AUTOMATED QUESTION GENERATION AND RESPONSE TRACKING

CROSS-REFERENCE TO RELATED APPLICATIONS

This patent application claims priority to U.S. Provisional Appl. Ser. No. 62/572,840, filed Oct. 16, 2017, which is incorporated herein by reference in its entirety.

BACKGROUND

Moderate memory loss is often considered to be a common effect of aging. Accurately measuring and monitoring memory loss is important in responding effectively to this development. For example, by monitoring memory loss of a patient over time, caregivers can detect deteriorations in the patient's memory capabilities in a manner that allows for effective and timely response and preparation. Moreover, monitoring memory loss over time provides valuable medical data that can be used to discern conditions of the patients and improve our understanding of memory loss.

However, effective and timely monitoring of memory loss over time requires a degree of engagement with the user that caregivers may not have. Moreover, when a patient is aging alone at home, it may be especially difficult to discern the pace at which the patient's memory capabilities are decaying. Nor is the patient guaranteed to have a good understanding and self-awareness of his/her decaying memory. Indeed, studies have shown that the inability of Alzheimer's disease patients to detect their memory loss is typically even greater than their memory deficit itself. See Dodson et al., *Alzheimer's Disease and Memory-Monitoring Impairment*, 49.9 NEUROPSYCHOLOGIA 2609 (July 2011).

Applicant has identified that there is a need for solutions that monitor memory loss with reduced caretaker involvement and without the need for patient self-awareness. Through applied effort, ingenuity, and innovation, the identified need has been solved by developing solutions that are included in embodiments of the present invention, many examples of which are described in detail herein.

BRIEF SUMMARY

In general, embodiments of the present invention provide methods, apparatus, systems, computing devices, computing entities, and/or the like for monitoring user cognitive capability (e.g., monitoring user memory loss). Certain embodiments utilize systems, methods, and computer program products that enable a caretaker to monitor cognitive capability of a user through conclusions drawn from interactions of the user with computing devices.

In accordance with one aspect, a method is provided. In one embodiment, the method comprises selecting a first question from a group of multiple questions to ask a user of a computing device based one or more attributes associated with each question in the group of multiple questions; receiving a first answer by the user of the computing device to the first question; determining, from the first answer, one or more behavioral attributes associated with user response to the first question; and determining, based on the one or more behavioral attributes, a cognitive capability of the user of the computing device.

In accordance with another aspect, a computer program product is provided. The computer program product may comprise at least one computer-readable storage medium having computer-readable program code portions stored therein, the computer-readable program code portions comprising executable portions configured to select a first question from a group of multiple questions to ask a user of a computing device based one or more attributes associated with each question in the group of multiple questions; receive a first answer by the user of the computing device to the first question; determine, from the first answer, one or more behavioral attributes associated with user response to the first question; and determine, based on the one or more behavioral attributes, a cognitive capability of the user of the computing device.

In accordance with yet another aspect, an apparatus comprising at least one processor and at least one memory including computer program code is provided. In one embodiment, the at least one memory and the computer program code may be configured to, with the processor, cause the apparatus to select a first question from a group of multiple questions to ask a user of a computing device based one or more attributes associated with each question in the group of multiple questions; receive a first answer by the user of the computing device to the first question; determine, from the first answer, one or more behavioral attributes associated with user response to the first question; and determine, based on the one or more behavioral attributes, a cognitive capability of the user of the computing device.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
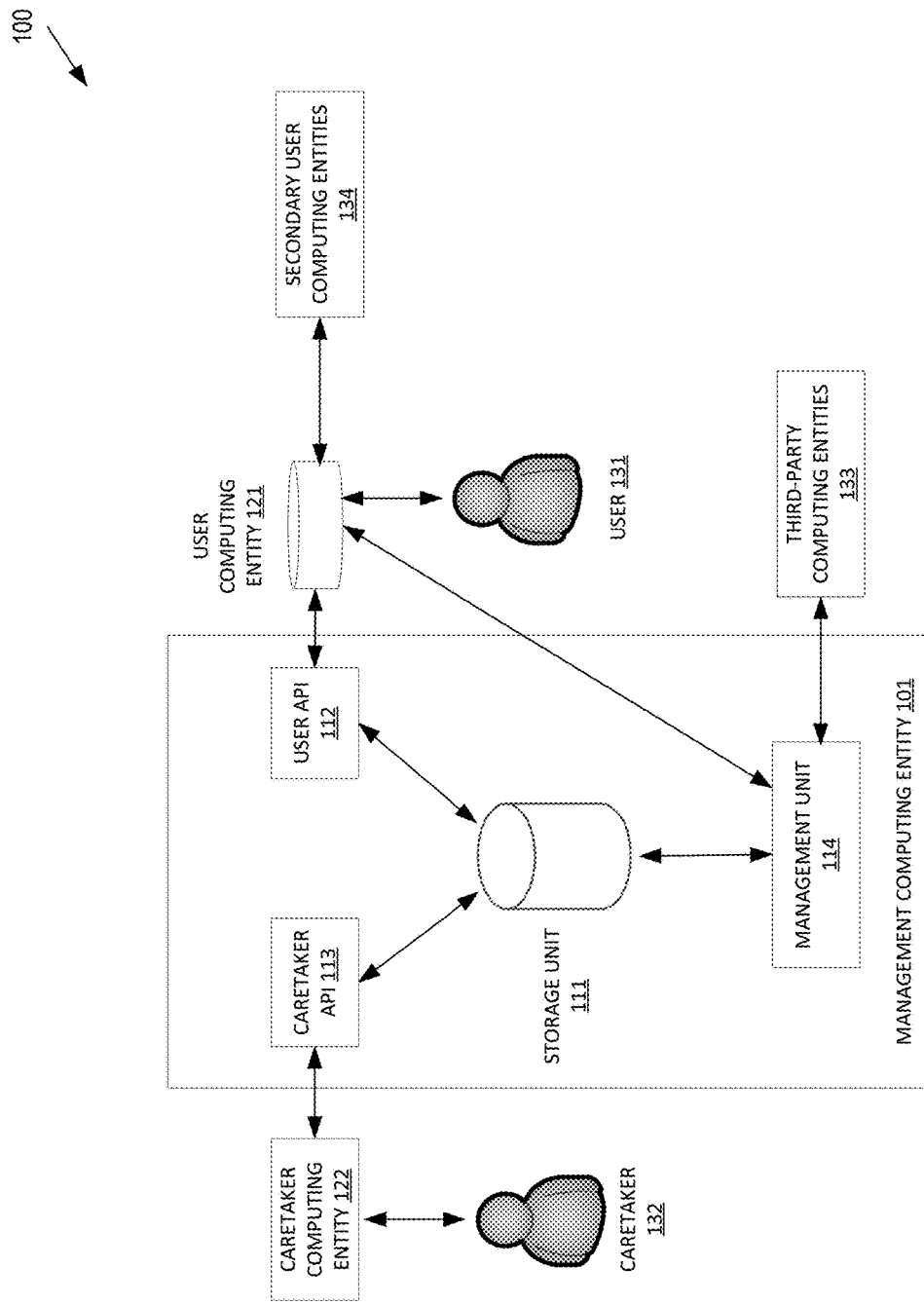
FIG. 1 is an exemplary overview of a system that can be used to practice embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

Moreover, while certain embodiments of the present invention are described with reference to monitoring memory loss, one of ordinary skill in the art will recognize that the disclosed concepts can be used to monitor other measures of cognitive capability in addition to or instead of memory loss.

I. OVERVIEW

Discussed herein methods, apparatus, systems, computing devices, computing entities, and/or the like for monitoring cognitive capability (e.g., monitoring memory loss). As will be recognized, however, the disclosed concepts can be used to reminder a user to perform any type of task and are not limited to a particular context.

A. Technical Problems

Various embodiments of the present invention seek to address the technical problem of monitoring memory loss of a patient with reduced caretaker involvement. Accurately measuring and monitoring memory loss is important in responding effectively to this development. For example, by monitoring memory loss of a patient over time, caregivers can detect deteriorations in the patient's memory capabilities in a manner that allows for effective and timely response and preparation. Moreover, monitoring memory loss over time provides valuable medical data that can be used to discern conditions of the patients and improve our understanding of memory loss. The task of monitoring memory loss is complicated by the fact that many memory loss patients often lack self-awareness of their memory loss and are unable to monitor their own memory loss. Thus, to effectively and accurately monitor memory loss, one may need to rely on observations of those other than the patient herself. However, for human observers to monitor memory loss, they need a level of engagement with the patient that may not always be suitable or practical. For example, a caretaker might need to ask different questions of the patient on a periodic basis, document answers to those questions, and infer a proper trend of patient memory capability from those answers. Such a high level of engagement and attention to the patient's condition may simply not be an option for many patients or may prove unduly resource-intensive. For example, when an individual is aging alone at home, it may be difficult to discern the pace at which the memory is declining and when a physician should be notified. Thus, there is a need for solutions for monitoring memory loss that require reduced caretaker involvement.

Monitoring memory loss with low caretaker involvement introduces further technical challenges associated with both data collection and analysis. Typical, caretaker-present scenarios for collecting data on the cognitive ability of a patient allows the caretaker to ensure that any memory-testing data collection exercises (such as question-answer sessions, memory-games, memory-related tasks, and/or the like) are relevant to the current state of the patient. When the caretaker's involvement is reduced however, other mechanisms are needed to ensure data collection exercises continue to collect relevant data regarding the patient's cognitive ability.

Moreover, any data collected through reduced caretaker involvement methodologies for assessing a patient's cognitive ability must be collected, stored, and appropriately analyzed to provide insightful indications of the patient's cognitive ability over time. Again, reducing the level of involvement of a caretaker in monitoring a patient's memory introduces significant risks that the results of a memory analysis may not accurately reflect the true cognitive ability of the patient. Accordingly, significant technical challenges exist for ensuring that the results of any data analysis performed accurately reflects the true cognitive ability of a patient.

B. Technical Solutions

Accordingly, various embodiments of the present invention address the technical problem of monitoring memory loss of a patient with reduced caretaker involvement by determining a cognitive capability of the user based on user interaction with a computing device. For example, various embodiments of the present invention relate to selecting a question to ask a user of a computing device; receiving an answer by the user to the first question; determining one or more behavioral attributes associated with user response to the question based on the answer; and determining a cognitive capability of the user based on the determined one or more behavioral attributes. By performing these steps or operations, the noted embodiments can eliminate the need to rely on caretakers to select questions, receive answers to the questions, determine behavioral attributes based on the answers; and determine cognitive capability based on the determined behavioral attributes. Thus, by determining a cognitive capability of the user based on user interaction with a computing device, various embodiments of the present invention address the technical problem of monitoring memory loss of a patient with reduced caretaker involvement.

In addition, various embodiments of the present invention address the technical problem of utilizing relevant data collection exercises for monitoring a patient's memory loss. To effectively monitor a patient's memory loss, a solution should generate questions that are sufficiently diverse to monitor different aspects of the patient's memory. This is in part because different aspects of a patient's memory may decay at different rates. For example, a patient may remember recent activities relatively well but have difficulty in remembering public information such as names of cities and towns. Evaluating a patient's memory loss with a diverse set of questions provides more detailed and meaningful analyses of the patient's memory loss, thus enabling a more effective response to the patient's needs and conditions. Thus, there is a need for solutions for monitoring memory loss that generate a diverse set of questions to monitor various aspects of a patient's memory. To address this need, various embodiments of the present invention relate to the generation of a diverse set of questions to monitor various aspects of a patient's memory using information obtained from third-party computer applications. Such third-party applications may include calendar applications, route planning applications, communication applications, news applications, etc.

For example, various embodiments of the present invention enable a memory loss monitoring application to generate a question about a previous social engagement of the patient based on information provided by a calendar application. As another example, various embodiments of the present invention enable a memory loss monitoring application to generate a question about a previous travel activity of the patient based on information provided by a route planning application. As yet another example, various embodiments of the present invention enable a memory loss monitoring application to generate a question about a previous communication activity of the patient based on information provided by a communication application. As a further example, various embodiments of the present invention enable a memory loss monitoring application to generate a question about a news report received by the patient based on information generated by a news application. Each of the noted applications generate information of a different type that may be used to monitor a different aspect of a patient's memory. Thus, by generating questions using information obtained from third-party computer applications, various embodiments of the present invention address the technical problem of generating a diverse set of questions to monitor various aspects of a patient's memory.

Furthermore, various embodiments of the present invention address the technical problem of ensuring relevance of the performed analysis to monitor memory capabilities. To effectively monitor a patient's memory loss, it is important to ask questions whose answers provide significant information about a patient's memory loss. For example, asking the same question too many times or asking a question that has lost its relevance because of passage of time may reduce the value of the questioning for monitoring the patient's memory loss. In those instances, a patient's correct or incorrect answer may not indicate much about the patient's memory capabilities. Thus, there is a need for solutions that select questions to enhance the value of answers to those question to monitoring a patient's memory loss. To address this need, various embodiments of the present invention relate to selecting questions to enhance the value of the corresponding answers to monitoring a patient's memory loss and to selecting questions based on one or more of question attributes and random selection.

For example, various embodiments of the present invention relate to determining desired attributes for a question, querying a group of multiple questions based on the desired attributes, and (if the query returns two or more questions) randomly selecting a question from the questions identified by the query. By selecting questions based on question attributes, various embodiments of the present invention enable a memory monitoring application to avoid questions that lack desired attributes. For example, various embodiments of the present invention enable querying a group of multiple questions to select questions from a category a, who have been asked less than b number of times, who have last been asked before time c, who have been generated by application or user d, and who have the difficulty level e or higher. Furthermore, randomly selecting questions reduces the chance for selecting repeated questions based on a preconfigured selection pattern. Thus, by selecting questions based on one or more of question attributes and random selection, various embodiments of the present invention address the technical problem of selecting questions to enhance the value of the corresponding answers to monitoring a patient's memory loss.

Moreover, various embodiments of the present invention address the technical problem of enhancing end user interaction with a memory loss monitoring computer application. Like other computer applications that interact with end-users, a memory loss monitoring application should aim to provide a natural user interaction experience. For example, a memory loss monitoring application should be mindful of a patient's preferences and desires in providing a user interaction experience. Otherwise, user experience may suffer. Indeed, providing a natural user interaction experience is especially important for memory loss monitoring applications, because such applications may engage users who suffer from diminished cognitive capability. Thus, there is no need for solutions that enhance user interaction with a memory loss monitoring computer application. Various embodiments of the present invention respond to this need by generating and/or selecting questions based on past history of user interaction with a user computing device. For example, various embodiments of the present invention relate to determining preferences of a user based on historical data indicating past user interaction with a computing device (e.g., the computing device used to ask questions from the user), and using such preferences to generate new questions for the user and/or select a question from an existing set of generated questions to ask the user. Integrating preferences of the user in question generation and/or question selection can make the user interaction experience with a memory loss monitoring application more natural and user-friendly. Thus, generating and/or selecting questions based on past history of user interaction with a user computing device, various embodiments of the present invention address the technical problem of enhancing end user interaction with a memory loss monitoring computer application.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

FIG. 1 provides an illustration of an exemplary embodiment of the present invention. FIG. 1 shows a system 100 including a management computing entity 101 interacting with a user computing entity 121, a caretaker computing entity 122, and one or more third-party computing entities 133. Each computing entity in the system 100 (i.e., the management computing entity 101, the user computing entity 121, the caretaker computing entity 122, the one or more third-party computing entities 133, and one or more secondary user computing entities 141) can include one computing device or multiple computing devices connected through one or more networks. Accordingly, each computing entity in the system 100 may include any suitable network server and/or other type of processing device. A network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.).

As depicted in the exemplary system 100 of FIG. 1, the user computing entity 121 is configured to enable a user 131 to interact with the management computing entity 101. In various embodiments, the user computing entity 121 may include a voice-assisted personal assistant computing device and/or an artificial intelligence (AI) computing device, such as an Amazon Echo, Amazon Echo Dot, Amazon Show, Google Home, and/or the like. Accordingly, the user computing entity 121 may be configured to provide and/or receive information/data from a user via an input/output mechanism, such as a display, a camera, a speaker, a voice-activated input, and/or the like. The user computing entity 121 may also include hardware and/or software resources configured to enable the management computing entity 101 to interact with a user computing device, such as resources configured to process calls to the Amazon Voice Service (AVS) application programming interface (API). An exemplary embodiment of a user computing entity 121 is described in greater detail below with reference to FIG. 2. The user computing entity 121 may interact with one or more secondary user computing entities 134. A secondary user computing entity 134 may be a computing device (e.g., an embedded computing device in furniture items or in an Internet of Things (IoT) system) that provides data and receives instructions from the user computing entity 121. The user computing entity 121 may provide some of the information obtained from the secondary user computing entities 134 to the management computing entity 101.

As further depicted in the exemplary system 100 of FIG. 1, the caretaker computing entity 122 is configured to enable a caretaker 132 to interact with the management computing entity 101. For example, the caretaker computing entity 122 may enable the caretaker 132 to generate questions stored by the management computing entity 101 and/or select questions that the management computing entity 101 will ask the user 131 by communicating with the user computing entity 121. As another example, the caretaker computing entity 122 may enable the caretaker 132 to obtain information relating to past interaction of the user 131 with the system 100 and/or past cognitive capability of the user 131. In various embodiments, the caretaker computing entity 122 may include a computer system maintained and used by a healthcare and/or elderly care provider institution. The caretaker computing entity 122 may include computing devices whose architecture is substantially similar to the architecture depicted in FIG. 2 or FIG. 3.

As further depicted in the exemplary system 100 of FIG. 1, the one or more third-party computing entities 133 are configured to provide various types of information to the management computing entity 101. For example, a third-party computing entity 133 may provide information to the management computing entity 101 that the management computing entity 401 can use to generate new questions. In various embodiments, a third party computing entity 133 is configured to store and/or execute one or more third-party computer applications, such as one or more third-party computer applications configured to interact with the user 131. Examples of third-party computer applications configured to provide information to the management computing entity 101 include calendar applications, route planning applications, communication applications, news applications, etc. A third-party computing entity 133 may generate information based on at least one of the interactions of the user 131 with the third-party computing entity 133, public information accessible through the World Wide Web, information manually entered by one or more end users of the third-party computing entity 133, etc.

As further depicted in the exemplary system 100 of FIG. 1, the management computing entity 101 includes a storage unit 111, a user API 112, a caretaker API 113, and a management unit 114. One or more components of the management computing entity 101 may reside on one computing device or on multiple computing devices connected through one or more networks.

The storage unit 111 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. In various embodiments, the storage unit 111 is configured to store questions, attributes for question, and metadata information about operation of the management computing entity 101. For example, the storage unit 111 may store one or more of the following attributes for a question: a prompt for a question, question category, question difficulty level, question generator's profile, acceptable answers for a question, hints for a question, attributes describing past user interaction with a question (e.g., a count of how many times the question has been asked before), etc. In various embodiments, the storage unit 111 is configured to store a database, such as a relational database. In various embodiments, the storage unit 111 is configured to store a file having a preconfigured format, such as JSON format. In various embodiments, metadata information about operation of the management computing entity 101 that is stored in the storage unit 111 may include information about interaction of the user 131 with the management computing entity 101. For example, the metadata information can include information about timing of a latest question retrieval by the user computing device 121.

The user API 112 is configured to enable the user computing entity 121 to interact with the management computing entity 101. For example, the user computing entity 121 may utilize a call to the user API 112 to request a question from the management computing entity 101. In response to such an API call, the user API 112 may retrieve prompt for a question from the storage unit 111 and provide the prompt to the user computing entity 121. For example, the user API 112 may select questions from a set of questions stored in the storage unit 111 based on one or more of: (i) filtering question using question attributes and a maintained logic for filtering questions using question attributes; and (ii) random selections of questions. As another example, the user computing entity 121 may utilize a call to the user API 112 to request a hint for a question from the management computing entity 101. In response to such an API call, the user API 112 may retrieve a hint for question from the storage unit 112 and provide the hint to the user computing entity 121.

In addition, the user computing entity 121 may utilize a call to the user API 112 to provide a user answer to a question to the management computing entity 101. In response to such an API call, the user API 112 may retrieve an acceptable answer to the question from the storage unit 112, analyze the user answer in the API call to determine whether the user answer matches an acceptable answer to the question, generate an output for the user computing entity 121 based on the result of the noted analysis, and record the result of the noted analysis in the storage unit 112 as part of the metadata about operation of the management computing entity 101. For example, if the user API 112 determines that the user answer to a question does not match an acceptable answer for the question, the user API 112 may generate an output for the user computing entity 121 that inquiries about whether the user 131 would like to receive a hint. As another example, if the user API 112 determines that the user answer to a question matches an acceptable answer for the question, the user API 112 may generate an output for the user computing entity 121 that inquires about whether the user 131 would like to receive a new question. As yet another example, if the user API 112 determines that the user answer to a question matches an acceptable answer for the question, the user API 112 may first query the storage database 111 for questions that (e.g., along with other query criteria) the user 131 has not been asked within a predefined amount of time (e.g., within the last n sessions) and, in response to determining that at least one question exists that matches the query criteria, the user API 112 may generate an output for the user computing entity 121 that inquires about whether the user 131 would like to receive a new question.

The management unit 114 is configured to affect and/or manage operation of the management computing entity 101 by changing questions, information, and/or attributes stored in the storage unit 111. For example, the management unit 114 can generate and add questions to the questions stored in the storage unit 111. The management unit 114 may generate questions based on information (e.g., questions, topics, categories, information about behavioral patterns of the user 131, information about communications of the user 131, publicly available information accessible through the World Wide Web) obtained from at least one third-party computing entity 133. The management unit 114 may generate questions based on information obtained from the third-party computing entities and/or the user computing entity 121. The information provided by the user computing entity 121 may include information received by the user computing entity 121 from the secondary user computing entities 134.

In various embodiments, the management unit 114 is further configured to transmit information to the user computing entity 121 based on the information stored in the storage unit 111. For example, the management unit 114 can use information stored in the storage unit 111 to determine that the user 131 has not requested a new question in a particular period of time and transmit information indicating a reminder message to the user computing entity 121.

A. Exemplary Management Computing Entity

Figure 2:
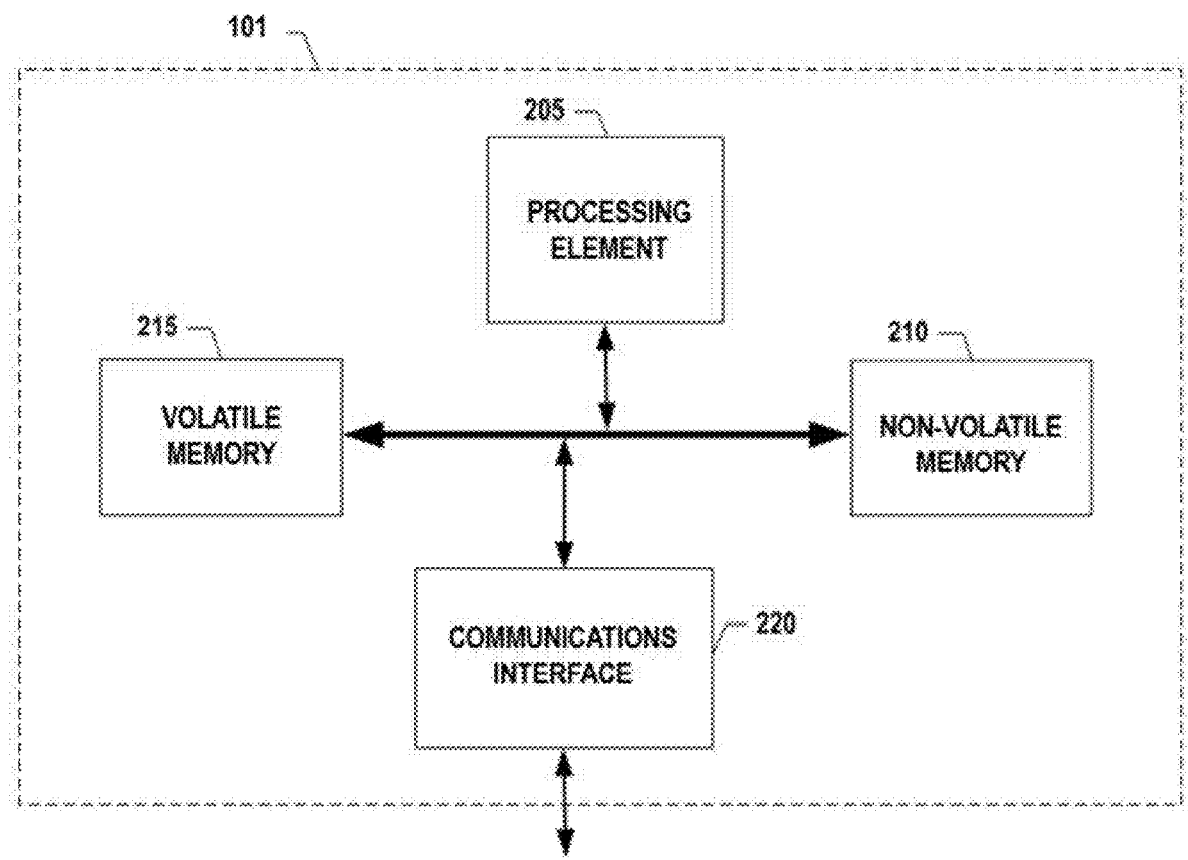
FIG. 2 illustrates an example management computing entity in accordance with some embodiments discussed herein.

FIG. 2 provides a schematic of a management computing entity 101 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, radio frequency identification (RFID) tags, ear pieces, scanners, televisions, dongles, cameras, wristbands, wearable items, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the management computing entity 101 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the management computing entity 101 may include or be in communication with one or more processing elements 205 (also referred to as processors, processing circuitry, and/or similar terms used herein interchangeably) that communicate with other elements within the management computing entity 101 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the management computing entity 101 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the management computing entity 101 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the management computing entity 101 with the assistance of the processing element 205 and operating system.

As indicated, in one embodiment, the management computing entity 101 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOC SIS), or any other wired transmission protocol. Similarly, the management computing entity 101 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown, the management computing entity 101 may include or be in communication with one or more input elements, such as a keyboard input, a mouse input, a touch screen/display input, motion input, movement input, audio input, pointing device input, joystick input, keypad input, and/or the like. The management computing entity 101 may also include or be in communication with one or more output elements (not shown), such as audio output, video output, screen/display output, motion output, movement output, and/or the like.

As will be appreciated, one or more of the management computing entity's 100 components may be located remotely from other management computing entity 101 components, such as in a distributed system. Furthermore, one or more of the components may be combined and additional components performing functions described herein may be included in the management computing entity 101. Thus, the management computing entity 101 can be adapted to accommodate a variety of needs and circumstances. As will be recognized, these architectures and descriptions are provided for exemplary purposes only and are not limiting to the various embodiments.

B. Exemplary User Computing Entity

Figure 3:
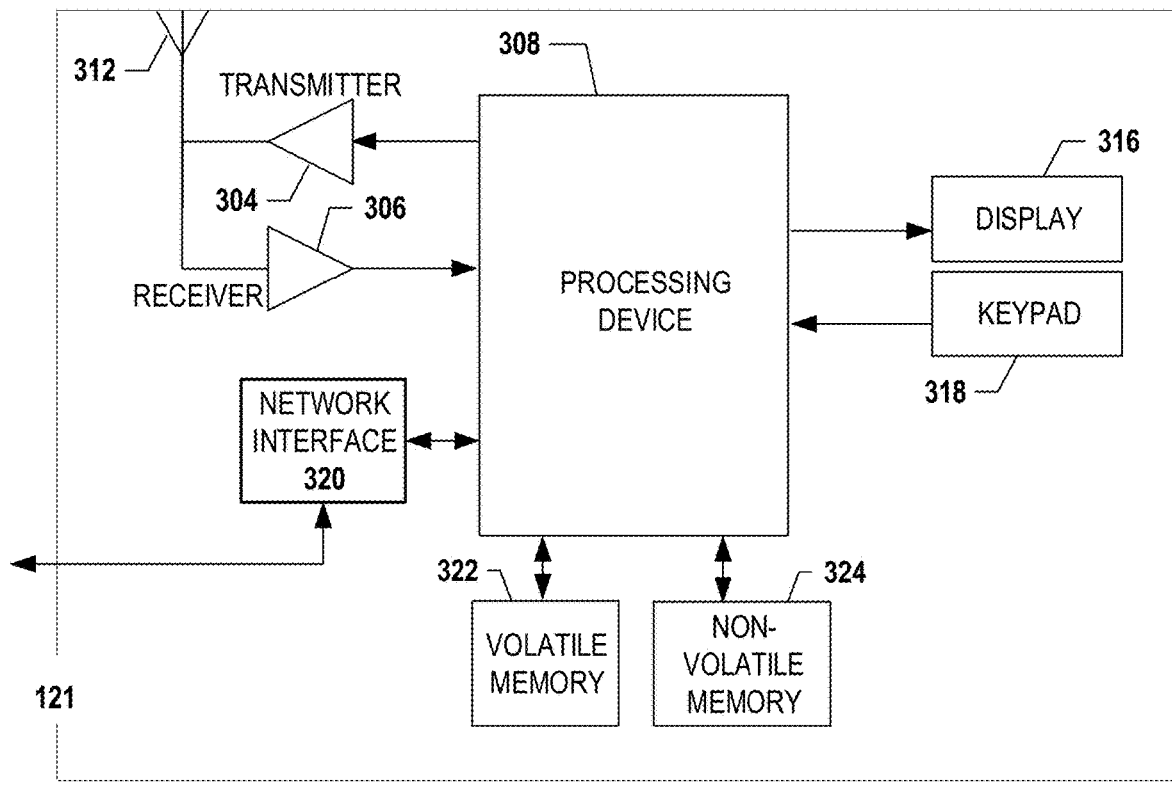
FIG. 3 illustrates an example user computing entity in accordance with some embodiments discussed herein.

A user may be an individual, a family, a company, an organization, an entity, a department within an organization, a representative of an organization and/or person, and/or the like. A user may operate a user computing entity 121 that includes one or more components that are functionally similar to those of the management computing entity 101. FIG. 3 provides an illustrative schematic representative of a user computing entity 121 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, RFID tags, ear pieces, scanners, televisions, dongles, cameras, wristbands, wearable items, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities 110 can be operated by various parties. As shown in FIG. 3, the user computing entity 121 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the user computing entity 121 may be capable of operating with one or more air interface standards, communication protocols, modulation types, and access types. More particularly, the user computing entity 121 may operate in accordance with any of a number of wireless communication standards and protocols, such as those described above with regard to the management computing entity 101. In a particular embodiment, the user computing entity 121 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity 121 may operate in accordance with multiple wired communication standards and protocols, such as those described above with regard to the management computing entity 101 via a network interface 320.

Via these communication standards and protocols, the user computing entity 121 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 121 can also download changes, add-ons, and updates, for instance, to its firmware, software (e.g., including executable instructions, applications, program modules), and operating system.

According to one embodiment, the user computing entity 121 may include location determining aspects, devices, modules, functionalities, and/or similar words used herein interchangeably. For example, the user computing entity 121 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information can be determined by triangulating the user computing entity's 121 position in connection with a variety of other systems, including cellular towers, Wi-Fi access points, and/or the like. Similarly, the user computing entity 121 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity 121 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the user computing entity 121 to interact with and/or cause display of information from the management computing entity 101, as described herein. The user input interface can comprise any of a number of devices or interfaces allowing the user computing entity 121 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the user computing entity 121 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity 121 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the user computing entity 121. As indicated, this may include a user application that is resident on the entity or accessible through a browser or other user interface for communicating with the management computing entity 101 and/or various other computing entities.

In another embodiment, the user computing entity 121 may include one or more components or functionality that are the same or similar to those of the management computing entity 101, as described in greater detail above. As will be recognized, these architectures and descriptions are provided for exemplary purposes only and are not limiting to the various embodiments.

In various embodiments, a user computing entity 121 may be embodied as an artificial intelligence (AI) computing entity, such as an Amazon Echo, Amazon Echo Dot, Amazon Show, Google Home, and/or the like. Accordingly, the user computing entity 121 may be configured to provide and/or receive information/data from a user via an input/output mechanism, such as a display, a camera, a speaker, a voice-activated input, and/or the like.

In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event. For example, the AI computing entity may be configured to retrieve and/or execute a particular program (e.g., the described cognitive evaluation game) in response to an audible, vocal request from a user (e.g., a user speaking an instruction to the AI computing entity to execute the particular program).

C. Exemplary Caretaker Computing Entity

The caretaker computing entity 122 may have a structure similar to a structure laid out in FIG. 3. For example, the caretaker computing entity 122 may include a computer system having processing units and memories. In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, RFID tags, ear pieces, scanners, televisions, dongles, cameras, wristbands, wearable items, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein.

D. Exemplary Secondary User Computing Entity

A secondary user computing entity 134 may have a structure similar to a structure laid out in FIG. 3. For example, a secondary user computing entity 134 may include a computer system having processing units and memories. In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, RFID tags, ear pieces, scanners, televisions, dongles, cameras, wristbands, wearable items, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein.

IV. EXEMPLARY SYSTEM OPERATION

The operation of various embodiments of the present invention will now be described. As discussed herein, various embodiments are directed to systems and methods for monitoring cognitive capability of a user, including generating questions for monitoring cognitive capability and selecting questions for monitoring cognitive capability. In various embodiments, cognitive capability of a user is monitored based on interactions of the user with a computing device.

A. Monitoring Cognitive Capability

As previously noted, various embodiments of the present invention monitor cognitive capability of a user by analyzing interactions of the user with a computing device (e.g., user computing entity 121). In some embodiments, analyzing interactions of a user with a computing device is limited to determining an answer to a question presented by the user and determining whether the answer matches an acceptable answer for a question (i.e., an accuracy level of user response to a computing device). In other embodiments, analyzing interactions of a user with a computing device may include determining other behavioral attributes associated with user interaction with a computing device, in addition to or instead of an accuracy level of user response to a computing device. This analysis may encompass considerations of other attributes of a user's response, such as the amount of time the user takes prior to responding, any spelling mistakes included within the user's answer, monitoring the user's facial expressions (e.g., via an integrated camera of the computing device), and/or the like.

Figure 4:
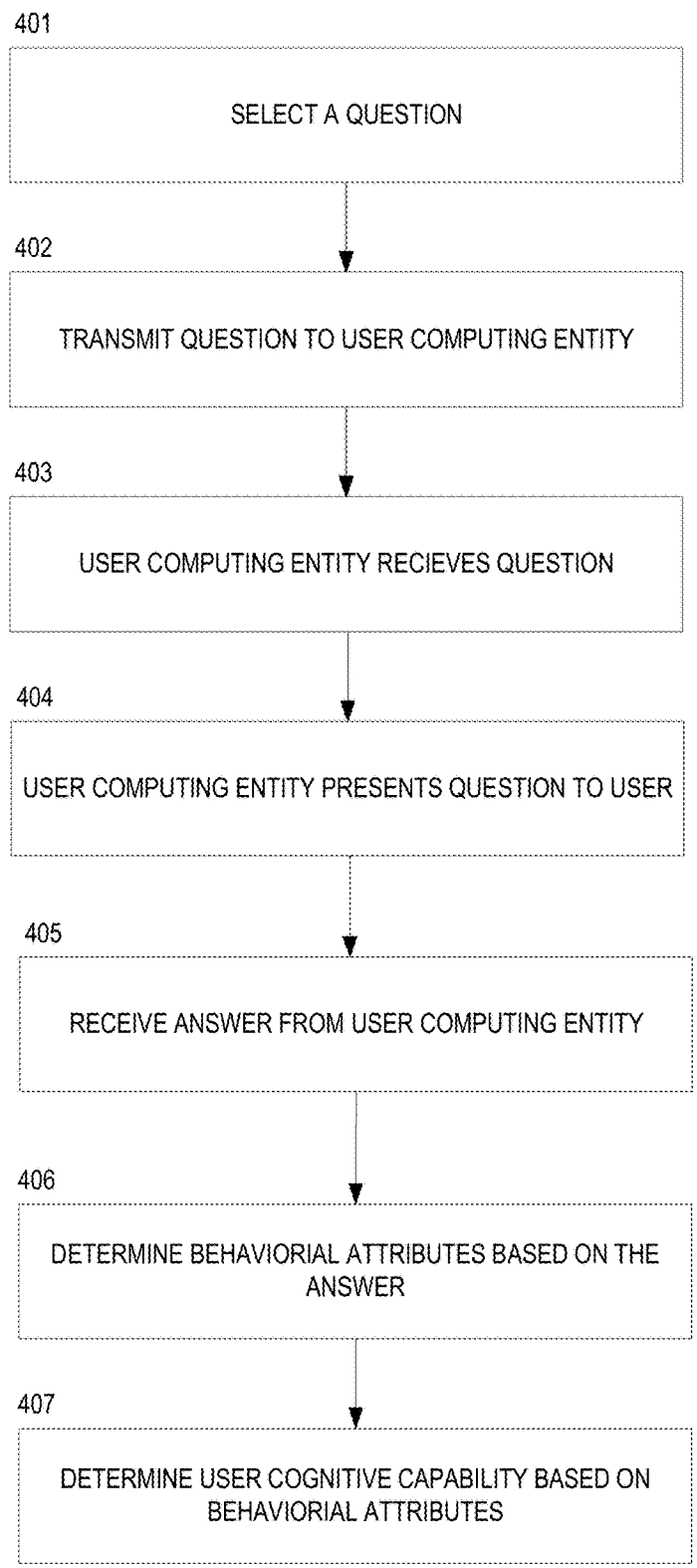
FIG. 4 illustrates a flow diagram of an example method for determining user cognitive capability in accordance with some embodiments discussed herein.

FIG. 4 illustrates a flow diagram of an example method for determining user cognitive capability in accordance with some embodiments discussed herein. Via the various steps of FIG. 4, a system (e.g., the system 100 of FIG. 1) can determine a cognitive capability of a user with reduced caretaker involvement by analyzing behavioral attributes associated with user response to a computing device. The methodology discussed in reference to FIG. 4 utilizes questions presented to the user, and those questions having one or more predefined correct answers that may be utilized as a reference point in determining the cognitive ability of the user. In certain embodiments, these questions may be multiple-choice questions (e.g., having a plurality of incorrect answer options and one or more correct answer options from which a user may select), free-entry questions (e.g., requiring a user to provide a freeform input (e.g., text-based input, drawing-based input, and/or the like) as an answer), fill-in-the-blank questions, matching questions, photo-based questions (e.g., requiring a user to describe/classify people/animals/objects shown in a photo), and/or the like).

These questions may be stored as a set of question attributes on the storage unit 111. The attributes of a question may include features of the question that are generally static (i.e., not prone to change) over the course of time, such as the prompt for a question, hints for a question, a category for a question etc. The attributes of a question may also include features of the question that are generally dynamic (i.e., prone to change) over the course of time, such as a number of times a question has been asked. Some attributes of a question may be determined based on one or more other attributes of a question. For example, a desirability score of the question (e.g., a prediction about how much a user finds the question desirable) may be determined based on a category of the question, a time in which the question was generated, etc. Question attributes may be stored using a data model, such as a relational data model or an object-oriented data model. The management unit 114 may index question attributes to facilitate targeted search and retrieval of those attributes.

As indicated in block 401, the system 100 (e.g., the management computing entity using the user API 112) selects a first question from a group of multiple questions to ask a user of a computing device. In various embodiments, the system 100 selects the first question based at least in part on one or more attributes associated with each question in the group of multiple questions. In some embodiments, the one or more attributes associated with each question in the group of multiple questions include at least one of a category of the respective question, a difficulty level of the respective question, a profile of a generator of the respective question, at least one acceptable answer associated with the first question, at least one hint associated with the respective question, a question type, and at least one attribute related to a history of interaction of the user with the respective question.

In some embodiments, the user computing entity 121 or a secondary user computing entity 134 selects the first question (e.g., using a question selection logic that depends on one or more selection inputs and one or more selection criteria). For example, the user computing entity 121 or a secondary user computing entity 134 may select the first question based on a user input (e.g., a user category selection). In some embodiments, the user computing entity 121 or a secondary user computing entity 134 provide a platform for a computer application related to the management computing entity 101 (e.g., an application client interface of the user API 112) to be installed and executed on the user computing entity 121 or a secondary user computing entity 134. In some of those embodiments, the installed and executed application selects the first question (e.g., using a question selection logic that depends on one or more selection inputs and one or more selection criteria).

In some embodiments, selecting the first question includes determining, based on at least one of historical data indicating past user 131 cognitive capability and one or more medical guidelines, one or more desired attributes for selecting a question; and querying the group of multiple questions based on the one or more desired attributes. Historical data may include data that indicate statistics about past user 131 cognitive capability. For example, historical data may indicate that the user 131 has had previous difficulty in responding to questions of a particular category. In response and in accordance with medical guidelines, the system 113 may select more questions from the particular category to ask the patient, e.g., to cause the patient to practice memory capabilities relating to the particular category. As another example, historical data may indicate that the user 131 has had previous success in responding to questions of a particular category. In response and in accordance with medical guidelines, the system 113 may select more questions from the particular category to ask the patient, e.g., to detect possible loss in memory capabilities relating to the particular category in the event that the patient starts to have difficulty in responding to questions from the particular category. Historical data may be generated by the management unit 114 through processing data describing past user 114 interactions with the management computing entity 101. Historical data may be stored on the storage unit 111.

In some of those embodiments, selecting the first question further includes randomly selecting the first question from a plurality of questions identified by the querying. For example, the system 100 may query a group of multiple questions to select questions from a category a, who have been asked less than b number of times, who have last been asked before time c, who have been generated by application or user d, and who have the difficulty level e or higher. If the query returns two or more results, the system 100 may select one of the two or more results based on a random selection process.

The specific technique used to query questions in accordance with the desired attributes may depend on the data format used to store question attributes. For example, if the question attributes are stored as a relational database, the system 100 may execute a relational selection operation (with the desired attributes being the parameters of the selection operation) to perform the query. On the other hand, if the question attributes are stored as an object-oriented database, the system 100 may perform one or more operations in accordance with an object-oriented algebra to perform the query. If the storage unit 111 includes indexing information associated with the storage of question attributes, the system 100 may use indexing information to perform the query. Performing the query may also entail a non-database operation. For example, the system 100 may generate a selection score for each question based on one or more question attributes and use the generated selection score to perform the query.

As indicated in block 403 the system 100 transmits the question to the user computing entity 122 using the user API 112. The system may transmit the question to the user computing entity 122 using an API associated with the user computing entity 122, such an AVS API. As indicated in block 404, the user computing entity 122 receives the transmitted question (e.g., using at least one of an API and a server associated with receiving communications to the user computing entity 122). As indicated in block 405, the user computing entity 122 presents the received question to the user 131. Questions may be presented using one or more computing devices. In some embodiments, a question prompt may have components with different formats, and each component may be presented using a different device. For example, a question prompt may ask a user to identify a person in a picture. In this example, the question prompt may include a voice component presented using a voice-enabled device and a picture component presented using a display device.

As indicated in block 402, the system 100 (using the user API 112) receives from the user computing entity 121 a first answer by the user 131 to the first question. In some embodiments, receiving the first answer includes making a call to an API associated with the user computing entity 121, such as the AVS API. The answer may include a representation of user 131 input to the user computing entity 121 (e.g., user 131 voice). In addition to the first answer, the user computing entity 121 may also supply information about user 131 behavior in interacting with the user computing entity 121 to the user API 112. For example, the user computing entity 121 may supply information about a delay between question presentation to the user 131 and user 131 answer, a typing speed of the user 131, a talking speed of the user 131, a measure of quality of user 131 speech, a measure of quality of user 131 writing, a measure quality of user 131 drawing, a measure of a spelling and/or grammar accuracy of the user 131, etc.

As indicated in block 407, the system 100 (using the user API 112) determines behavioral attributes based on one or more behavioral attributes associated with user response to the first question. In some embodiments, the one or more behavioral attributes associated with user response to the first question include at least one of an accuracy level of the user response, a time duration of the user response, a decipherability of the user response, whether the user response included a request for hints, and a language of the user response. In some embodiments, the user response to the first question is a voice response and the one or more behavioral attributes associated with the user response to the first question include at least one of a tone of the user response and a volume of the user response. For example, the system 100 may estimate a time of question presentation based on a time of transmission of question to the user computing entity 122 and determine a time duration of the user response based on data about a timing of user response and the estimated time of question presentation.

In certain embodiments, the decipherability of user response is a measure of how much the user response is comprehensible. The appropriate mechanism for determining decipherability may depend on the type of response the user provides. For example, a typed response may be reviewed for typographical and/or grammatical errors (e.g., based on an integrated or otherwise accessible text review system), a drawn or hand-written response may be reviewed for legibility, a measure of how straight various lines are, or other characteristics of the user-provided input. In other instances, decipherability of an audio-based user response (e.g., a voice-response) may be determined by first generating a representation of the user response (e.g., a transcribed version of user voice input) to determine a meaning from the user response and a value indicating the system's confidence in the determined meaning. The system may then determine the decipherability of the user response based on the value indicating the system's confidence in the determined meaning. In various embodiments, the system may use data indicating decipherability of user response to determine cognitive abilities of the user (e.g., a neurological disability manifested by mistyping or speaking difficulties; a learning disability manifested by a failure to learn concepts and meanings; a memory loss effect manifested by forgetting words).

In general, particular behavioral attributes associated with user-computing device interactions may be more relevant to determining some cognitive capabilities than others. For example, time duration of user response and decipherability of the user response may be particularly relevant to determining nervous system disorders (e.g., of the types seen in Parkinson's disease patients). Moreover, some behavioral attributes may have particular significance to determining cognitive capabilities of users with particular conditions and/or historical backgrounds. For example, language of user response may be particularly relevant to determining cognitive capabilities of bilingual and multilingual users.

As indicated in block 404, the system determines a cognitive capability of the user of the computing device based on the one or more behavioral attributes. In some embodiments, determining a cognitive capability of the user includes determining one or more measures of cognitive capability of the user. Examples of measures of cognitive capability includes memory loss measures, nervous disorder measures, learning disability measures, emotional disability measures, etc. In some embodiments, determining the cognitive capability of the user includes comparing the one or more behavioral attributes associated with the user response to the first question to historical data indicating past user behavioral attributes. For example, the system may determine that the user has a reduced memory capability if the ability of the user to respond to questions in a category have gone done by a threshold amount.

In some embodiments, the system determines the cognitive capability of the user based on behavioral attributes by processing the behavioral attributes using a trained machine learning model. For example, the trained machine learning model may have been trained (e.g., by using a gradient descent algorithm) using training data that includes past behavioral attributes of a user as training inputs and corresponding past determinations about cognitive capability of the user (e.g., based on medical records) as target training outputs. For example, the system may use temporal proximity of an interaction with a computing device and a medical visit as a basis for determining that medical records obtained during the medical visit can correspond to target training outputs for the input training data determined based on the interaction.

The system may generate one or more outputs based on a determined cognitive ability of the user. For example, the system may generate one or more alerts to be provided to caretakers 132 upon determining that a user's 131 cognitive ability satisfies one or more alert criteria. As other examples, the system may generate one or more reports (e.g., periodic reports) indicative of the user's 131 cognitive ability over time, such that a caretaker 132 may monitor any changes in the user's 131 cognitive ability.

In some embodiments, the system determines one or more measures of cognitive ability relating to a patient's self-awareness of his/her own health conditions. These determined measures of cognitive ability may be based on the patient's answers to questions that pertain to the ability of the patient to manage the patient's health conditions. Examples of questions that pertain to the ability of the patient to manage the patient's health conditions include questions about management of a particular disease state, questions about medication use and/or medication therapy management, questions about self-care (e.g., things to do after a doctor's appointment or discharge from a facility), etc. In response to determining that a patient lacks a cognitive ability related to an ability of the patient to manage the patient's health conditions, the system may recommend, schedule, and/or provide a patient care service related to the missing cognitive ability. Examples of such patient care services include disease state management, medication therapy management, self-care recommendations, etc.

B. Generating Questions

Question generation may be manual, automatic, or both. For example, a caretaker 132 or other user may manually enter new questions or may provide information regarding various events, facts, and/or the like that may be translated into a question via a caretaker computing entity 122 in communication with a management computing entity 101. As another example, the management unit 114 (or another computer application executing via a computing device) may automatically generate questions based on at least one of interactions of a user 131 with a third-party computing entity 133, public information accessible through the World Wide Web, information manually entered by end users of a third-party computing entity 133, etc. As yet another example, a computer application may generate questions based on information obtained from one or more other computer applications. Generating a question may include generating attributes for the question (e.g., the prompt for the question, the answer for the question, the hint for the question, etc.). In various embodiments, after being generated, a question and the question's attributes are stored in a storage unit. For those questions provided by a caretaker 132, the caretaker 132 may provide various attributes regarding the provided question (e.g., via input to the caretaker computing entity 122). In other embodiments, the management computing entity 101 may be configured to generate at least a portion of the attributes for a caretaker-generated question. For example, the management computing entity 101 may be configured to classify the difficulty of a caretaker-provided question (e.g., based on a determined question type, content of the question, the identity of the caretaker 132 who provided the question, and/or the like). In certain embodiments, the management computing entity 101 may be configured to utilized machine learning or other algorithms for providing various attributes of a question, thereby enabling the management computing entity 101 to effectively utilize various question selection algorithms when providing questions to the user computing entity 121.

Figure 5:
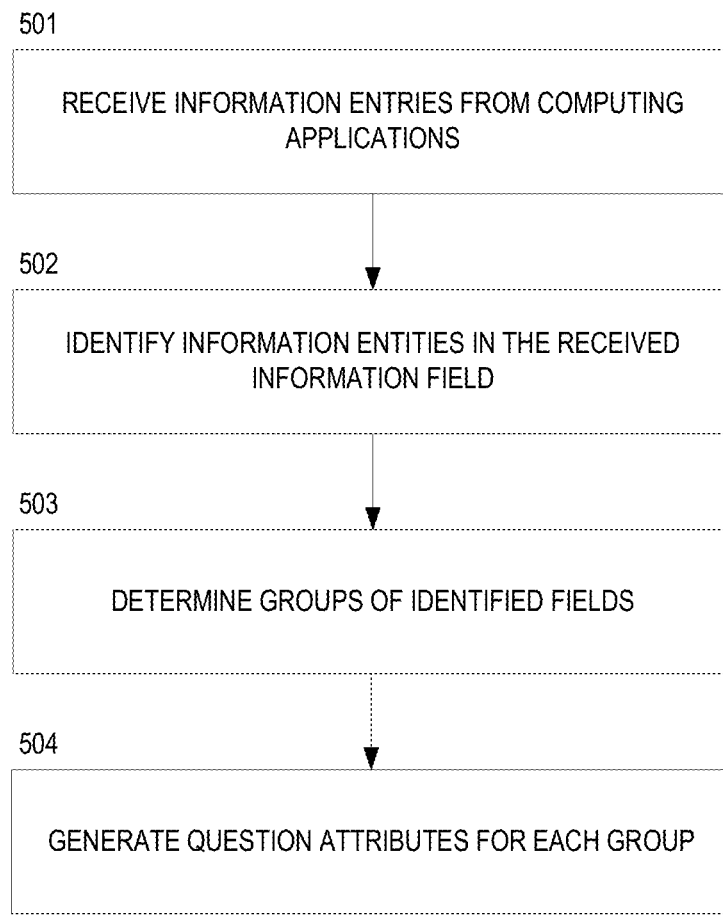
FIG. 5 illustrates a flow diagram of an example method for generating questions to evaluate user cognitive capability based on information obtained from one or more computer applications in accordance with some embodiments discussed herein.

FIG. 5 illustrates a flow diagram of an example method for automatically generating questions to evaluate user cognitive capability based on information obtained from one or more computer applications in accordance with some embodiments discussed herein. Via the various steps of FIG. 5, a system (e.g., the system 100 of FIG. 1) can generate a diverse set of questions by using information obtained from one or more computer applications.

As indicated in block 501, the system receives information entries from one or more computer applications. A computer application may be configured to interact with a user. Examples of third-party computer applications includes calendar applications, route planning applications, communication applications, news applications, etc. A computer application may generate information based on at least one of the interactions of a user with computer application, public information accessible through the World Wide Web, information manually entered by one or more end users of the computer application, etc. In some embodiments, receiving an information entry from a computer application includes accessing a server associated with the computer application using an API configured to enable such an access. Information may be received from the one or more computer applications by periodic retrieval (e.g., by the management computing entity 101 "pulling" information from the one or more computer applications) or in realtime, as the information is generated at the computer applications (e.g., by the computer application "pushing" information to the management computing entity 101. Moreover, the API utilized for receipt of information at the management computing entity 101 ensures that information is provided in a normalized, fielded context, thereby ensuring that the management computing entity 101 is capable of identifying appropriate facts for inclusion within a prompt and for identifying a correct answer to the question. In some embodiments, the system maintains logic and information needed to authenticate that the system is a legitimate recipient of information entries associated with a computer application.

As indicated in block 502, the system identifies information fields in the information entries received from computer applications. The system may identify information fields in the received information entries using one or more of a maintained logic for identifying information fields in an information entity and a natural language processing module. Some received information entries may have a structured format that is conducive to identifying one or more information fields. For example, an information entity associated with a route planning application may identify a time and a geographic designation of a destination of a travel. Other information entries may wholly or partially lack this structured format. In various embodiments, the system may utilize a natural language processing module (e.g., a natural language processing module trained using data associated with past interaction of a user with a computing device) to determine information fields in the received information entries.

As indicated in block 503, the system determines groups of identified information fields that can be aggregated to form a basis for a question. For example, to generate a question regarding a destination of a particular travel activity that occurred yesterday afternoon, the system may determine a group including an identified information field about timing of the particular travel activity and an identified information field about the destination of the travel activity. In some embodiments, the system may determine groups that include information fields identified based on information entries received from two or more computer applications. For example, the system may determine based on an information entry received from a route planning application that the user was at a location a at time b. The system may also determine based on an information entry received from a financial transaction application that the user bought an item c at a time d. The system may determine a correlation between the two information entries by determining that times b and d are within a threshold proximity of each other. In response to determining this correlation, the system may group information entries a and c to ask question about what the user bought at location a.

As indicated in block 504, the system generates question attributes for each determined group of identified information fields. In some embodiments, the system determines whether each information field in the determined group of identified information fields relates to one or more of a prompt for a question, an acceptable answer to the question, and a hint for the question. The system can then use the information fields determined to be related to the prompt for a question and a language model to generate the prompt; use the information fields determined to be related to an acceptable answer to the question prompt to generate the acceptable answer; and use the information fields determined to be related to a hint for the question to generate the hint.

These questions may be stored as a set of question attributes on a storage unit. The attributes of a question may include features of the question that are generally static (i.e., not prone to change) over the course of time, such as the prompt for a question, hints for a question, a category for a question etc. The attributes of a question may also include features of the question that are generally dynamic (i.e., prone to change) over the course of time, such as a number of times a question has been asked. Some attributes of a question may be determined based on one or more other attributes of a question. For example, a desirability score of the question (e.g., a prediction about how much a user finds the question desirable) may be determined based on a category of the question, a time in which the question was generated, etc. Question attributes may be stored using a data model, such as a relational data model or an object-oriented data model. A management unit may index question attributes to facilitate targeted search and retrieval of those attributes.

C. Selecting Questions from Generated Questions

Questions may be selected from the storage unit 111 for eventual presentation to a user 131. Question selection may be based on one or more filtering questions based on question attributes and random selection of question. In various embodiments, the system selects a question based at least in part on one or more attributes associated with each question in a group of multiple questions. In some embodiments, the one or more attributes associated with each question in the group of multiple questions include at least one of a category of the respective question, a difficulty level of the respective question, a profile of a generator of the respective question, at least one acceptable answer associated with the first question, at least one hint associated with the respective question, and at least one attribute related to a history of interaction of the user with the respective question.

In some embodiments, selecting a question includes determining, based on at least one of historical data indicating past user cognitive capability (e.g., based on a historical performance of the user answering questions presented by the system; the time interval since the last time the user answered questions presented by the system; a historical trend of the user in answering questions presented by the system; and/or the like) and one or more medical guidelines, one or more desired attributes for selecting a question; and querying the group of multiple questions based on the one or more desired attributes. In some of those embodiments, selecting the first question further includes randomly selecting the first question from a plurality of questions identified by the querying. For example, the system may query a group of multiple questions to select questions from a category a, who have been asked less than b number of times, who have last been asked before time c, who have been generated by application or user d, and who have the difficulty level e or higher.

In some embodiments, the system calculates a desirability score for a question based on one or more of a timing of question generation, a number of times a question have been asked, and preferences of a user. For example, the system may reduce desirability score for a question (e.g., using a decay model) as the question becomes older based on a timing of question generation. As another example, the system may reduce desirability score for a question each time the user is asked the particular question and/or other questions determined to be similar to the question. As yet another example, the system may set the desirability score of the question based on one or more preferences of the user.

The system may use the desirability score to select questions. In some embodiments, the system may select a question having the highest desirability score to ask the patient. In some other embodiments, the system may use a weighed random algorithm to select a question, where the weight of the question is determined based on the desirability score of the question. In yet other embodiments, the system selects a candidate question based on a question selection technique (e.g., a combination of filtering and random selection), but refuses to present the candidate question to the user if the desirability score for the question falls below a threshold value. In some of the noted embodiments, in response to determining that the desirability score of a selected candidate question falls below a threshold value, the system selects a new candidate question using a question selection technique.

The system may further use the desirability score to remove questions from a repository of available questions. For example, in various embodiments, the system removes a question if one or more attributes of the question satisfy a removal criteria. In some of those embodiments, one removal criteria may be determined at least in part based on whether the desirability score for a question falls below a threshold level.

D. Predictive Behavioral Analysis

In various embodiments, the present invention relates to predicting preferences of the user based on past user interactions with a computer device and using those preferences in operating a system configured to monitor cognitive capability of a user, e.g., in question generation and/or question selection by such a system. For example, various embodiments relate to determining desired attributes of generated questions, desired attributes of selected questions, and/or desirability scores for generated questions based on historical data indicating past user interactions with the computing device.

Figure 6:
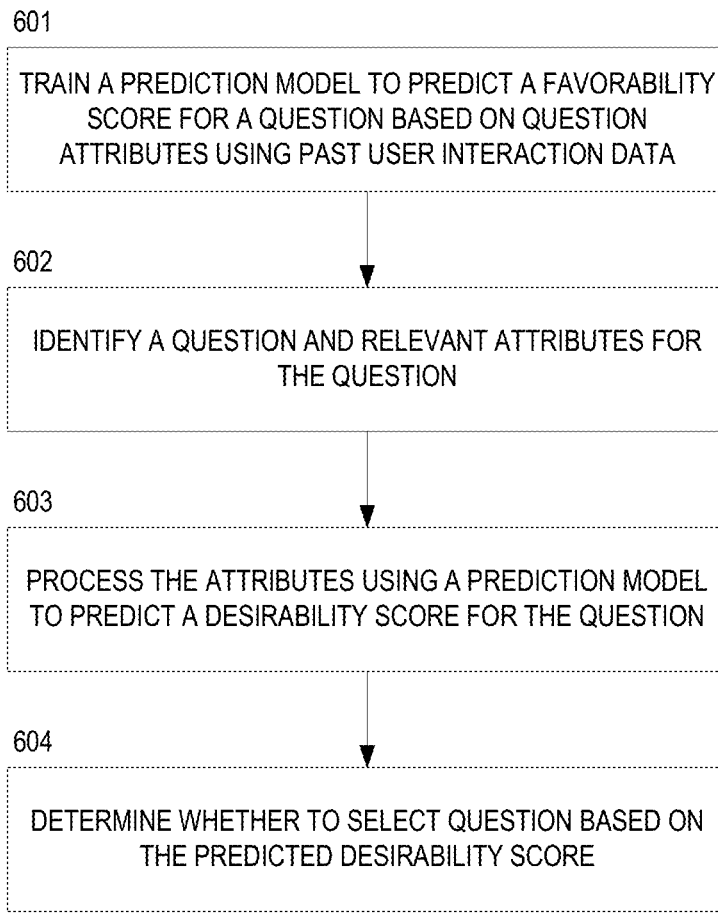
FIG. 6 illustrates a flow diagram of an example method for selecting questions to evaluate user cognitive capability in accordance with some embodiments discussed herein.

FIG. 6 illustrates a flow diagram of an example method for selecting questions to evaluate user cognitive capability in accordance with some embodiments discussed herein. Via the various steps of FIG. 6, a system (e.g., the system of FIG. 1) can predict preferences of a user based on past user interactions with a computing device and use the predicted preferences to select questions to ask the user.

As indicated in block 601, the system trains a prediction model to predict a favorability score for a question based on question attributes and using past user interaction data. For example, the system may compute how often has the user in the past requested and/or answered questions having particular attributes and use such computed values as target training outputs for a machine learning model. The system may also use combinations of question attributes as training inputs. Using the training inputs and target training outputs, the system may train the machine learning model, for example by using a gradient descent algorithm.

As indicated in block 602, the system identifies a question and relevant attributes for a question. In some embodiments, the relevant attributes for predicting a desirability score for a question include only some, but not all, of the attributes of the question. In other embodiments, the system may generate new relevant attributes for the question by combining and/or weighing some or all of the attributes for the question. For example, the system may scale a question category for a question by a large weight value to increase the importance of the question category in predicting a desirability score for the question.

As indicated in block 603, the system processes the relevant attributes using the prediction model to determine a desirability score the question. As indicated above, the prediction model could be a machine learning model such as a model using one or more of linear regression, polynomial regression, logistic regression, feedforward neural networks, recurrent neural networks, etc. The system may provide the relevant attributes as an input to the prediction model and obtain the determined desirability score obtained by the prediction model via processing of the relevant attributes.

As indicated in block 604, the system determines whether to select a question based on the determined desirability score for the question. For example, the system may determine whether the determined desirability score exceeds a threshold value and select the question in response to determining that the desirability score exceeds the threshold value. As another example, the system may select the question from a group of question if the desirability score of the question exceeds desirability scores of other questions in the group.

E. Presenting Questions

Question prompts may be presented using one or more computing devices. For example, the user API 112 of the management computing entity 112 may provide one or more question attributes (e.g., the question prompt) for a question to the user computing entity 121 (e.g., through one or more of an API and/or a server associated with interacting with the user computing entity 121). The user computing entity 121 may then present the question to the user 131 using one or more computing entities. In some embodiments, a question prompt may have components with different formats, and each component may be presented using a different device. For example, a question prompt may ask a user to identify a person in a picture. In this example, the question prompt may include a voice component presented using a voice-enabled device and a picture component presented using a display device.

F. Analyzing Cognitive Ability Determinations

The system may use a determination about a cognitive ability of a user to make conclusions about a cognitive state of the user, including a change in the cognitive state of the user over time. For example, in some embodiments, the system compares the one or more behavioral attributes associated with the user response to the first question to historical data indicating past user behavioral attributes. In some of those embodiments, comparing the one or more behavioral attributes associated with the user response to the first question to the historical data indicating past user behavioral attributes includes determining, from the historical data, a past average associated with interaction of the user with the group of multiple questions; determining, based on the user response to the first question, a moving average associated with interaction of the user with the group of multiple questions; and comparing the moving average to the past average.

The system may make conclusions about health of the user based on trends in cognitive ability determinations of the same kind over time. For example, the system may determine increases or reductions over time in memory loss determinations, learning disability determinations, and/or neurological disability determinations. In addition, the system may make conclusions about health of the user based on cognitive ability determinations of different kinds. For example, the system may use memory loss determinations and neurological disability determinations to determine that increased memory loss of a patient is a likely result of larger neurological issues. Moreover, the system may make conclusions about health of the user based on cognitive ability determinations and non-cognitive health data. For example, the system may use genetic data and memory loss determinations to determine early stages of a cognitive disability in a user.

The system may make conclusions derived in whole or in part from the cognitive ability determinations available to caretakers, medical professionals, intelligent medical computer applications, machine learning modules. In various embodiments, the system uses the determinations to allow medical professionals to obtain data about cognitive ability of their patients. In some embodiments, the system may use cognitive ability determinations in scheduling appointments and/or initiating drug deliveries.

The system make use conclusions derived in whole or in part from the cognitive ability determinations to perform actions related to and/or addressing a patient's health. For example, in response to determining that a patient lacks a cognitive ability related to an ability of the patient to manage the patient's health conditions, the system may recommend, schedule, and/or provide a patient care service related to the missing cognitive ability. Examples of such patient care services include disease state management, medication therapy management, self-care recommendations, etc.

As another example, the system may use the cognitive ability determinations to provide output intended to direct attention of the patient towards particular disease management, therapy management, assistance, and/or advocacy programs. As yet another example, if cognitive ability determinations indicate that a patient's cognitive ability has fallen below a threshold value, the system may generate alerts and/or notifications regarding particular disease management, therapy management, assistance, and/or advocacy programs. In some embodiments, the system may use cognitive ability determinations (e.g., the question categories associated with each cognitive ability determination) to generate custom alerts and/or reminders for the user (e.g., alerts and/or reminders to management of a condition or therapy).

As a further example, the system may use cognitive ability determinations to determine optimal visits from different caregivers, and accordingly recommend, require, schedule, and/or monitor caregiver services appointments. As a yet further example, the system may use cognitive ability determinations before and after a caregiver appointment to monitor a measure of effectiveness of particular caregiver services intended to be delivered during the caregiver appointment.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, the foregoing description provides various examples of utilizing systems and methods for monitoring cognitive capability of a user. However, it should be understood that various embodiments of the systems and methods discussed herein may be utilized for providing reminders of any activity, such as exercising, eating healthy snacks, performing a particular task, calling another individual, and/or the like.

The invention claimed is:

1. A computer-implemented method for monitoring user memory loss, the method comprising:
   retrieving, by a computing entity, a plurality of questions, wherein each of the plurality of questions is associated with a timing of question generation, wherein the plurality of questions comprise: (i) a first question that is determined based at least in part on a previous travel activity of a user as determined based at least in part on information provided by a route planning application, (ii) a second question that is determined based at least in part on a previous communication activity of the user as determined based at least in part on information provided by a communication application, and (iii) a third question that is determined based at least in part on a news report received by the user as determined based at least in part on information provided by a news application;
   generating, by the computing entity, a predicted desirability score for each question of the plurality of questions using a prediction model, wherein the predicted desirability score for each question of the plurality of questions is based at least in part on at least one question attribute, and wherein the prediction model is a machine learning model that is trained using training data describing past behavioral attributes of one or more past users as training inputs and corresponding past determinations about user memory loss measures of the one or more past users as target training outputs;
   for each question of the plurality of questions, reducing, by the computing entity, the predicted desirability score for the question by:
      (i) reducing the predicted desirability score as the question becomes older based at least in part on the timing of question generation; and
      (ii) reducing the predicted desirability score for the question each time of a plurality of times that the question is presented to the user;
   selecting, by the computing entity, a first candidate question from the plurality of questions that has a highest predicted desirability score;
   adopting, by the computing entity, the first candidate question as a selected question;
   determining, by the computing entity, whether the predicted desirability score for the first candidate question satisfies a predicted desirability score threshold;
   in response to determining that the predicted desirability score for the first candidate question fails to satisfy the predicted desirability score threshold: (i) selecting, by the computing entity, a second candidate question from the plurality of questions based at least in part on a randomly-selected question that is selected from a subset of the plurality of questions, wherein: (a) all of the questions in the subset have a defined category, have been asked less than a defined number of times, have last been asked before a defined time, have been generated by a defined application, and have a defined difficulty level or higher, and (b) historical data associated with the user indicates that the user has had previous difficulty in responding to questions related to the defined category, and (ii) adopting, by the computing entity, the second candidate question instead of the first candidate question as the selected question;
   transmitting, by the computing entity, the selected question to the user computing entity for presentation to the user;
   receiving, by the computing entity, a first answer, wherein the first answer was provided as user input by the user of the user computing entity in response to the selected question;
   determining, by the computing entity and based at least in part on the first answer, one or more response attributes associated with the user input provided by the user in response to the selected question;
   determining, by the computing entity and based at least in part on processing the one or more response attributes, a memory loss measure of the user of the computing entity, wherein determining the memory loss measure of the user comprises comparing the one or more response attributes associated with the user response to the selected question to historical data indicating one or more of the same response attributes associated with the user; and performing, by the computing entity, one or more caregiver visitation schedule management operations for the user based at least in part on the memory loss measure of the user.

2. The method of claim 1, further comprising:
generating, by the computing entity and based at least in part on the one or more response attributes associated with the user input provided by the user in response to the selected question, a new question to add to the plurality of questions; and
adding, by the computing entity, the new question to the plurality of questions.

3. The method of claim 1, further comprising:
determining, by the computing entity and based at least in part on the predicted desirability score associated with each question of the plurality of questions, that at least one question from the plurality of questions satisfies predetermined removal criteria; and
removing, by the computing entity, the at least one question from the plurality of questions.

4. The method of claim 3, wherein determining that the at least one question from the plurality of questions satisfies the predetermined removal criteria comprises:
identifying, by the computing entity, one or more attributes of the at least one question relating to a past interaction of the user with the at least one question; and
determining, by the computing entity and based at least in part on the one or more attributes of the at least one question, that the past interaction of the user with the at least one question exceeds a threshold amount of user interaction associated with the predetermined removal criteria.

5. The method of claim 1, wherein each predicted desirability score for a question of the plurality of questions is adjusted based at least in part on at least one of a category of the question, a difficulty level of the question, a profile of a generator of the question, at least one acceptable answer associated with the question, at least one hint associated with the question, and at least one attribute related to a history of interaction of the user with the question.

6. The method of claim 1, wherein the one or more response attributes associated with the user input provided by the user in response to the selected question include at least one of an accuracy level of the user response, a time duration of the user response, a decipherability of the user response, whether the user response included a request for hints, and a language of the user response.

7. The method of claim 1, wherein determining the memory loss measure of the user comprises comparing the one or more response attributes associated with the user response to the selected question to historical data indicating past user response attributes.

8. The method of claim 7, wherein comparing the one or more response attributes associated with the user response to the selected question to the historical data indicating past user response attributes further comprises:
determining, by the computing entity and from the historical data, a past average associated with interaction of the user with the plurality of questions;
determining, by the computing entity and based at least in part on the user response to the selected question, a moving average associated with interaction of the user with the plurality of questions; and
comparing, by the computing entity, the moving average to the past average.

9. The method of claim 1, wherein the user response to the selected question is a voice response and the one or more response attributes associated with the user response to the selected question include at least one of a tone of the user response and a volume of the user response.

10. The method of claim 9, wherein the selected question is presented to the user as a voice prompt.

11. The method of claim 10, wherein the voice prompt is presented to the user using a voice-enabled personal assistant software.

12. The method of claim 1, wherein the selected question is presented to the user as an image via a display device of the user computing entity.

13. The method of claim 1, wherein the plurality of questions are generated based at least in part on information obtained from one or more computing applications.

14. An apparatus for monitoring user memory loss, the apparatus comprising at least one processor and at least one memory including program code, the at least one memory and the program code configured to, with the processor, cause the apparatus to at least:
retrieve a plurality of questions, wherein each of the plurality of questions is associated with a timing of question generation, wherein the plurality of questions comprise: (i) a first question that is determined based at least in part on a previous travel activity of a user as determined based at least in part on information provided by a route planning application, (ii) a second question that is determined based at least in part on a previous communication activity of the user as determined based at least in part on information provided by a communication application, and (iii) a third question that is determined based at least in part on a news report received by the user as determined based at least in part on information provided by a news application;
generate a predicted desirability score for each question of the plurality of questions using a prediction model, wherein the predicted desirability score for each question of the plurality of questions is based at least in part on at least one question attribute, and wherein the prediction model is a machine learning model that is trained using training data describing past behavioral attributes of one or more past users as training inputs and corresponding past determinations about user memory loss measures of the one or more past users as target training outputs;
for each question of the plurality of questions, reduce the predicted desirability score for the question by:
(i) reducing the predicted desirability score as the question becomes older based at least in part on the timing of question generation; and
(ii) reducing the predicted desirability score for the question each time of a plurality of times that the question is presented to the user;
select a first candidate question from the plurality of questions that has a highest predicted desirability score;
adopt the first candidate question as a selected question;
determine whether the predicted desirability score for the first candidate question satisfies a predicted desirability score threshold;
in response to determining that the predicted desirability score for the first candidate question fails to satisfy the predicted desirability score threshold: (i) select a second candidate question from the plurality of questions based at least in part on a randomly-selected question that is selected from a subset of the plurality of questions, wherein: (a) all of the questions in the subset have a defined category, have been asked less than a defined number of times, have last been asked before a defined time, have been generated by a defined application, and have a defined difficulty level or higher, and (b) historical data associated with the user indicates that the user has had previous difficulty in responding to questions related to the defined category, and (ii) adopt the second candidate question instead of the first candidate question as the selected question;
transmit the selected question to the user computing entity for presentation to the user;
receive a first answer provided, wherein the first answer was provided as user input by the user of the user computing entity in response to the selected question;
determine, based at least in part on the first answer, one or more response attributes associated with the user input provided by the user in response to the selected question;
determine, based at least in part on processing the one or more response attributes, a memory loss measure of the user of the computing entity, wherein the determination of the memory loss measure of the user comprises comparing the one or more response attributes associated with the user response to the selected question to historical data indicating one or more of the same response attributes associated with the user; and
perform one or more caregiver visitation schedule management operations for the user based at least in part on the memory loss measure of the user.

15. The apparatus of claim 14, wherein the program code is further configured to, with the processor, cause the apparatus to at least:
generate, based at least in part on the one or more response attributes associated with the user input provided by the user in response to the selected question, a new question to add to the plurality of questions; and
add the new question to the plurality of questions.

16. The apparatus of claim 14, wherein the program code is further configured to, with the processor, cause the apparatus to at least:
determine, based at least in part on the predicted desirability score associated with each question of the plurality of questions, that at least one question from the plurality of questions satisfies predetermined removal criteria; and
remove the at least one question from the plurality of questions.

17. A non-transitory computer-readable storage medium for monitoring user memory loss, the computer-readable storage medium storing program code instructions that, when executed, cause a computing entity to:
retrieve a plurality of questions, wherein each of the plurality of questions is associated with a timing of question generation, wherein the plurality of questions comprise: (i) a first question that is determined based at least in part on a previous travel activity of a user as determined based at least in part on information provided by a route planning application, (ii) a second question that is determined based at least in part on a previous communication activity of the user as determined based at least in part on information provided by a communication application, and (iii) a third question that is determined based at least in part on a news report received by the user as determined based at least in part on information provided by a news application;
generate a predicted desirability score for each question of the plurality of questions using a prediction model, wherein the predicted desirability score for each question of the plurality of questions is based at least in part on at least one question attribute, and wherein the prediction model is a machine learning model that is trained using training data describing past behavioral attributes of one or more past users as training inputs and corresponding past determinations about user memory loss measures of the one or more past users as target training outputs;
for each question of the plurality of questions, reduce the predicted desirability score for the question by:
(i) reducing the predicted desirability score as the question becomes older based at least in part on the timing of question generation; and
(ii) reducing the desirability score for the question each time of a plurality of times that the question is presented to the user;
select a first candidate question from the plurality of questions that has a highest predicted desirability score;
adopt the first candidate question as a selected question;
determine whether the predicted desirability score for the first candidate question satisfies a predicted desirability score threshold;
in response to determining that the predicted desirability score for the first candidate question fails to satisfy the predicted desirability score threshold: (i) select a second candidate question from the plurality of questions based at least in part on a randomly-selected question that is selected from a subset of the plurality of questions, wherein: (a) all of the questions in the subset have a defined category, have been asked less than a defined number of times, have last been asked before a defined time, have been generated by a defined application, and have a defined difficulty level or higher, and (b) historical data associated with the user indicates that the user has had previous difficulty in responding to questions related to the defined category, and (ii) adopt the second candidate question instead of the first candidate question as the selected question;
transmit the selected question to the user computing entity for presentation to the user;
receive a first answer provided, wherein the first answer was provided as user input by the user of the user computing entity in response to the selected question;
determine, based at least in part on the first answer, one or more response attributes associated with the user input provided by the user in response to the selected question;
determine, based at least in part on processing the one or more response attributes, a memory loss measure of the user of the computing entity, wherein the determination of the memory loss measure of the user comprises comparing the one or more response attributes associated with the user response to the selected question to historical data indicating one or more of the same response attributes associated with the user; and
perform one or more caregiver visitation schedule management operations for the user based at least in part on the memory loss measure of the user.

18. The non-transitory computer-readable storage medium of claim 17, wherein the program code instructions, when executed, cause the computing entity to further:
generate, based at least in part on the one or more response attributes associated with the user input provided by the user in response to the first question, a new question to add to the plurality of questions; and
add the new question to the plurality of questions.

19. The method of claim 1 further comprising:
receiving, from a third-party computing entity, information comprising at least one interaction between a user and the third-party computing entity;
generating, by a computing entity, at least one question based at least in part on the at least one interaction between a user and the third-party computing entity; and
storing, by the computing entity, the new question and one or more associated question attributes.

* * * * *